(12) United States Patent
Kim et al.

(10) Patent No.: US 8,827,455 B2
(45) Date of Patent: Sep. 9, 2014

(54) AUTOMATIC REFRACTO-KERATOMETER

(71) Applicant: Huvitz Co., Ltd., Gunpo-si (KR)

(72) Inventors: Hyoung-UK Kim, Anyang-si (KR); Joong-Jae Lee, Anyang-si (KR)

(73) Assignee: Huvitz Co., Ltd., Gunpo-Si (KR)

( * ) Notice: Subject to any disclaimer, the term of this patent is extended or adjusted under 35 U.S.C. 154(b) by 0 days.

(21) Appl. No.: 14/086,106

(22) Filed: Nov. 21, 2013

(65) Prior Publication Data

US 2014/0078470 A1    Mar. 20, 2014

Related U.S. Application Data

(62) Division of application No. 13/325,977, filed on Dec. 14, 2011, now Pat. No. 8,727,534.

(30) Foreign Application Priority Data

Jan. 24, 2011  (KR) .......................... 10-2011-0006984
Feb. 7, 2011   (KR) .......................... 10-2011-0010700

(51) Int. Cl.
*A61B 3/00* (2006.01)
*A61B 3/103* (2006.01)
*A61B 3/15* (2006.01)
*A61B 3/107* (2006.01)

(52) U.S. Cl.
CPC ............... *A61B 3/0025* (2013.01); *A61B 3/103* (2013.01); *A61B 3/152* (2013.01); *A61B 3/107* (2013.01)
USPC .......................................................... 351/247

(58) Field of Classification Search
USPC .......................................................... 351/247
See application file for complete search history.

(56) References Cited

U.S. PATENT DOCUMENTS

2012/0062844 A1* 3/2012 Svochak et al. ............... 351/247

* cited by examiner

*Primary Examiner* — Mahidere Sahle
(74) *Attorney, Agent, or Firm* — Lexyoume IP Meister, PLLC

(57) ABSTRACT

An auto refracto-keratometer not only produces a black-and-white image for observing the alignment of eyes to be examined using an infrared illumination light but also has a color observation optical system for observing a condition of eyes to be examined using color-illumination light. The auto refracto-keratometer comprises an infrared optical system for examining an alignment and corneal curvature of eyes to be examined; a fogging optical system for relaxing accommodation of the eyes; a measuring optical system for measuring refractive power of the eyes; and a color observation optical system having a visible light source for emitting at least one visible light to the eyes and a 2-dimensional imaging device for detecting image of visible light reflected by the eyes.

5 Claims, 8 Drawing Sheets

AUTOMATIC REFRACTO-KERATOMETER

This application is a Divisional Application of U.S. patent application Ser. No. 13/325,977 filed on Dec. 14, 2011, which claims the priority benefits of Korean patent application Ser. No. 10-2011-0006984 filed on Jan. 24, 2011, and Korean patent application Ser. No. 10-2011-0010700 filed on Feb. 7, 2011. All disclosures of the Korean Patent applications are incorporated herein by reference.

FIELD OF THE INVENTION

This invention relates to an automatic refracto-keratometer, and more particularly, to an automatic refracto-keratometer which not only produces a black-and-white image for observing an alignment of an eye to be examined using an infrared illumination light but also has a color observation optical system for observing the eye using a color illumination light. This invention also relates to a method for evaluating a fitting state of contact lens with an image processing technique for detecting a dye pattern by using the automatic ref racto-keratometer.

BACKGROUNDS OF THE INVENTION

An automatic refracto-keratometer is a precise measuring-instrument used in the field of ophthalmic optics, in which optical equipments, electronic equipments, precise machines and computer programs are integrated. The auto ref racto-keratometer accurately, quickly and objectively measures physical features of an eye such as a refractive power, an astigmatism power, an astigmatism axis and so on, with optical and electronic systems. Thus, the refracto-keratometer is generally used for a prescription of eyeglass or contact lens. FIG. 1 is an optical circuit showing a configuration of a conventional automatic refracto-keratometer. As shown in FIG. 1, the conventional ref racto-keratometer includes an infrared optical system 10 for examining an alignment and a corneal curvature of an eye 5 to be examined, a fogging optical system 30 for removing an accommodation power of the eye 5 so that the eye 5 is properly relaxed, and a refractive power measuring optical system 50 for measuring a refractive power of the eye 5. In operation, for examining the alignment and the corneal curvature of the eye 5, an infrared light is emitted from a mire ring light source 12 of the infrared optical system 10. The infrared light is reflected by the eye 5 and then reflected by a dichroic mirror 14. The reflected light passes through a relay lens 16, is reflected by an infrared reflecting mirror (a hot mirror) 17, passes through an image forming lens 18 (a relay lens or a collimating lens), and forms an infrared image of the eye 5 on a 2-dimensional imaging device 20. FIG. 2 is a photograph showing an infrared image of the eye 5 formed on the imaging device 20. With the infrared image, the position of the eye 5 is adjusted to be aligned to a central axis of the refracto-keratometer, and a corneal curvature of the eye 5 is also measured from the size of the infrared ring image. The measured corneal curvature is used for prescription of a contact lens When the eye 5 is aligned to the central axis of the refracto-keratometer, an interim refractive power of the eye 5 is measured with the refractive power measuring optical system 50. Specifically, an infrared light for measuring the refractive power is emitted from an infrared light source 52, and the infrared measuring light passes through a badal lens 54 for focusing the infrared measuring light on a main surface of the eye 5, is reflected by a reflecting mirror 56 and a polarization beam splitter 58 for polarizing the infrared measuring light, and focused on a retina of the eye 5. A signal light, which is reflected and scattered on the retina of the eye 5, passes through the polarization beam splitter 58, an objective lens 60, an image forming lens 62 and a micro-lens array 64. The objective lens 60 focuses the signal light, the image forming lens 62 collimates or converges the signal light, and the micro-lens array 64 splits the converged signal light into multiple signal lights and also focuses the split signal lights. The split signal lights form images of the signal lights on a 2-dimensional imaging device 66 as shown in FIG. 3. Then, a process and control unit 7 calculates the interim refractive power of the eye 5 from the images of the split signal lights.

After the interim refractive power is calculated, the fogging optical system 30 is operated to relax the eye 5. In detail, a white light is emitted from a white light source 32 and then passes through an image layer 34 to produce an image for fixing the eye's attention and also for relaxing the eye's accommodation power. The image produced at the image layer 34 passes through an adjusting lens 36 for focusing the image according to the refractive power of the eye 5, a reflecting mirror 38, and relay lenses 40, 16, and then the image is reflected by the dichroic mirror 14 and directed to the retina of the eye 5. Thus, the image of the image layer 34 is clearly formed on the retina of the eye 5. After forming the image of the image layer 34 on the retina of the eye 5, the adjusting lens 36 is controlled so that the image of the image layer 34 is not focused on the retina of the eye 5 (that is, the image of the image layer 34 becomes unclear to the eye 5), and thereby the accommodation power of the eye 5 is removed. When the accommodation power of the eye 5 is removed, the above-mentioned refractive power measuring process is repeated to obtain the target and accurate refractive power of the eye 5.

Besides the corneal curvature and the refractive power of the eye 5 obtained with the refracto-keratometer shown in FIG. 1, a fitting state of the eye 5 and a contact lens should be examined for a proper prescription of a contact lens. As shown in FIG. 4, to examine the fitting state, a dye, such as a fluorescent substance, is injected to the eye 5, a contact lens is placed on the eye 5, and a blue light, which is sensitive to the fluorescent substance, is irradiated to the eye 5. Then the fitting state between the eye 5 and the contact lens is observed with a slit beam microscope. Generally, the prescription of a contact lens requires several steps, such as a medical examination by interview with a contact lens user, an examination of a front eye, a corneal curvature measurement, a selection of a base-curve, an evaluation of the fitting state, and so on. The interview is conducted to obtain information which is necessary for the prescription of a contact lens. The examination of a front eye is conducted to check the conditions of an eyelid, an eyelash, a cornea, and so on. The corneal curvature measurement is conducted to obtain the curvature of the center of a cornea with a keratometer, a topographer and so on. The base-curve is determined to select a suitable contact lens for the cornea of the eye. The evaluation of the fitting state is conducted to check whether a contact lens properly fits to the eye. The fitting state can be evaluated by examining a dye pattern, movements and positions of contact lens, and so on with an instrument such as a button lamp, a slit beam microscope and so on. In accordance with such evaluation results, suitable contact lens can be prescribed.

In the dye pattern examination, a dye, such as a fluorescent substance, specifically, fluorescein is injected to an eye, a contact lens is placed on the eye, and the fitting state between the eye and the contact lens is observed with a slit beam microscope. When the fluorescein contacts with tear in the eye, the color of fluorescein changes to green, and the locations of tear, specifically the locations of tear between the cornea and the contact lens can be clearly observed, and the fitting state of the contact lens can be properly evaluated. FIGS. 5a~5c are photographs showing the fitting states of a contact lens on a model eye. The fitting can be generally classified into a steep state (FIG. 5a), a flat state (FIG. 5b) and an alignment state (FIG. 5c). The steep state indicates that a contact lens having a small curvature is selected. In this case, a periphery of the contact lens contacts to the cornea and the tear gathers in the center part of the eye. Thus, tear is not properly circulated, impurities cannot be properly removed from eye, and oxygen cannot be properly supplied to the eye. The flat state indicates that a contact lens having a large curvature is selected. In this case, a large amount of tear is located around the periphery of the contact lens, and the center part of the contact lens contacts to the cornea. Thus, the contact lens user may feel inconvenience in eyelid movements and a corneal xerosis. Furthermore, the contact lens can be dislocated from its original location by the movement of the eye. The alignment state is an ideal state in which a proper amount of tear is uniformly dispersed between the cornea and the contact lens. The slit beam microscope for observing the fluorescein patterns includes an optical part and a mechanical part, and may further includes an electronic part such as a camera. In the slit beam microscope, the fitting state may be directly observed with an eyepiece lens of the optical part or indirectly observed with the camera or a monitor of the electronic part. The examiner observes the fluorescein patterns and determines and evaluates the fitting state of the contact lens on the basis of his or her experience and knowledge.

In the conventional contact lens fitting, at least two apparatuses for a measurement and an observation are necessary. Especially, the observation apparatus simply displays a magnified image of an eye, but doest not provide any useful information. In addition, since at least two apparatuses are necessary, the arrangement of the apparatus is complicated, and a skilled person is necessary for using the apparatus. Thus, the contact lens prescription process cannot be effectively carried out with the prior apparatus.

SUMMARY OF THE INVENTION

Therefore, it is an object of the present invention to provide a ref racto-keratometer for observing an eye with a color illumination light as well as an infrared illumination light.

It is other object of the present invention to provide a refracto-keratometer having a color observation optical system for observing a fitting state between an eye and a contact lens with a color image.

It is another object of the present invention to provide a method for evaluating a fitting state of a contact lens which performs both of a measurement and an observation for a prescription of a contact lens with a single apparatus.

It is still another object of the present invention to provide a method for evaluating a fitting state of a contact lens which improves efficiency and productivity in prescribing a contact lens.

In order to achieve these and other objects, the present invention provides a ref racto-keratometer comprising: an infrared optical system for examining an alignment of an eye and for measuring a corneal curvature of the eye; a fogging optical system for relaxing the eye's accommodation power; a refractive power measuring optical system for measuring a refractive power of the eye; and a color observation optical system having a visible light source for emitting at least one visible light to the eye and a 2-dimensional imaging device for detecting the eye's image irradiated with the visible light.

The present invention also provides a method for evaluating a fitting state of a contact lens, the method comprising the steps of: detecting a pupil area and an iris area in an eye; obtaining a dye image showing a location of a dye in the eye by irradiating a visible light which can detect the dye to the eye; converting the dye image to a single color image whose intensities are proportional to amounts of the dye; detecting a boundary, a center and a radius of a contact lens placed on the eye from the single color image; dividing an area of the contact lens into two parts, a central part W and peripheral parts W1, W2, ... Wi ... Wn, the central part W being an inner circle area having a radius of ¼ to ½ times of the radius of the contact lens and the peripheral parts W1, W2, ... Wi ... Wn being the remainder of the central part W; and calculating a dying degree Ck of the central part W and comparing the calculated dying degree Ck with a predetermined range to evaluate a fitting state of the contact lens.

Preferably, the dying degree Ck is a ratio of an area Wg of pixels having intensities higher than a predetermined value in the central part W with respect to the area of the central part W. Also preferably, the fitting state can be evaluated by calculating a dying degree Ci of the peripheral part Wi, and comparing the dying degree Ci with a predetermined range. Also preferably, the fitting state can be evaluated by calculating a dying degree Ci of the peripheral part Wi, calculating an edge width Ei which is a minimum distance between a center of gravity of pixels having color intensities higher than a predetermined value and the boundary of the contact lens, and the comparing the dying degree Ci and the edge width Ei with predetermined ranges.

An eye and/or a contact lens placed on the eye are observed with the color observation optical system in the refracto-keratometer of the present invention. The prescription of a contact lens can be carried out effectively with the ref racto-keratometer of the present invention, and an additional apparatus is not necessary for examining the fitting state of the contact lens. In addition, by the present invention, the contact lens fitting state can be consistently evaluated regardless of the examiner's experience or skill.

DETAILED DESCRIPTION OF THE INVENTION

A more complete appreciation of the invention, and many of the attendant advantages thereof, will be better appreciated by reference to the following detailed description.

Figure 1:
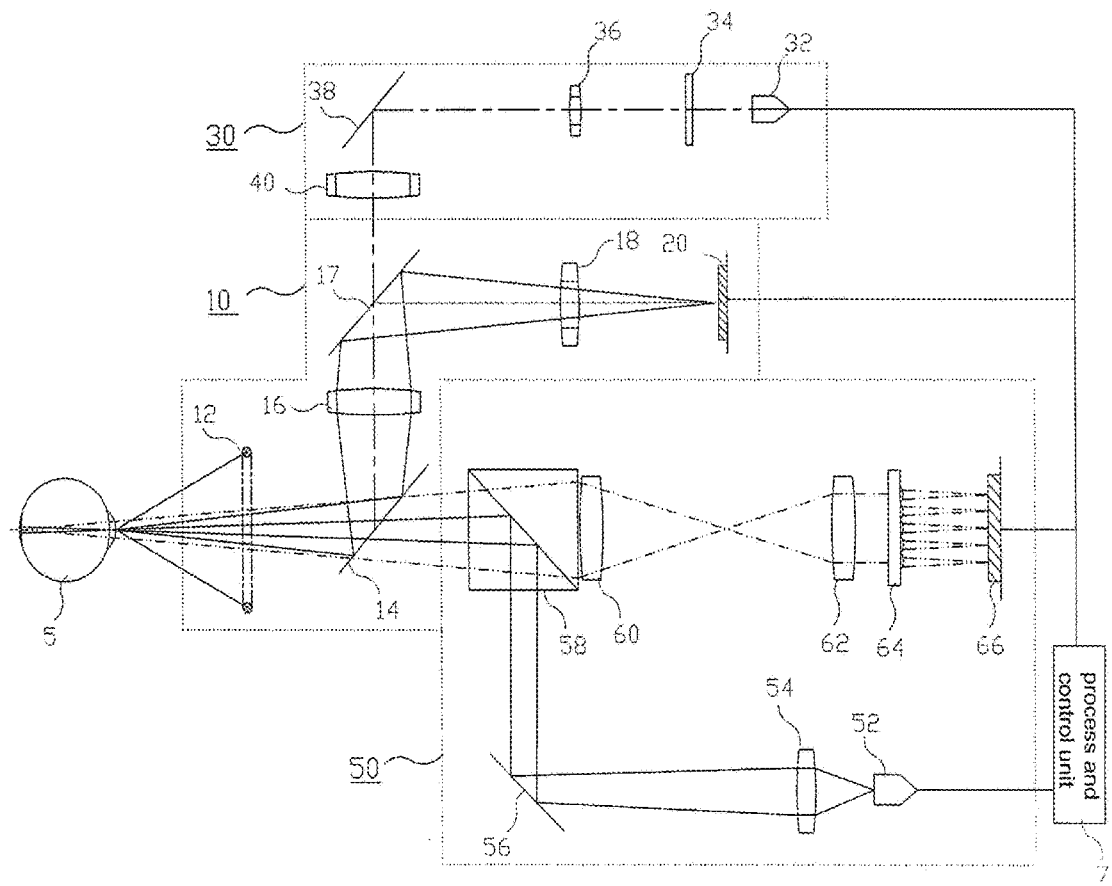
FIG. 1 is an optical circuit showing a configuration of a conventional automatic ref racto-keratometer.
Figure 6:
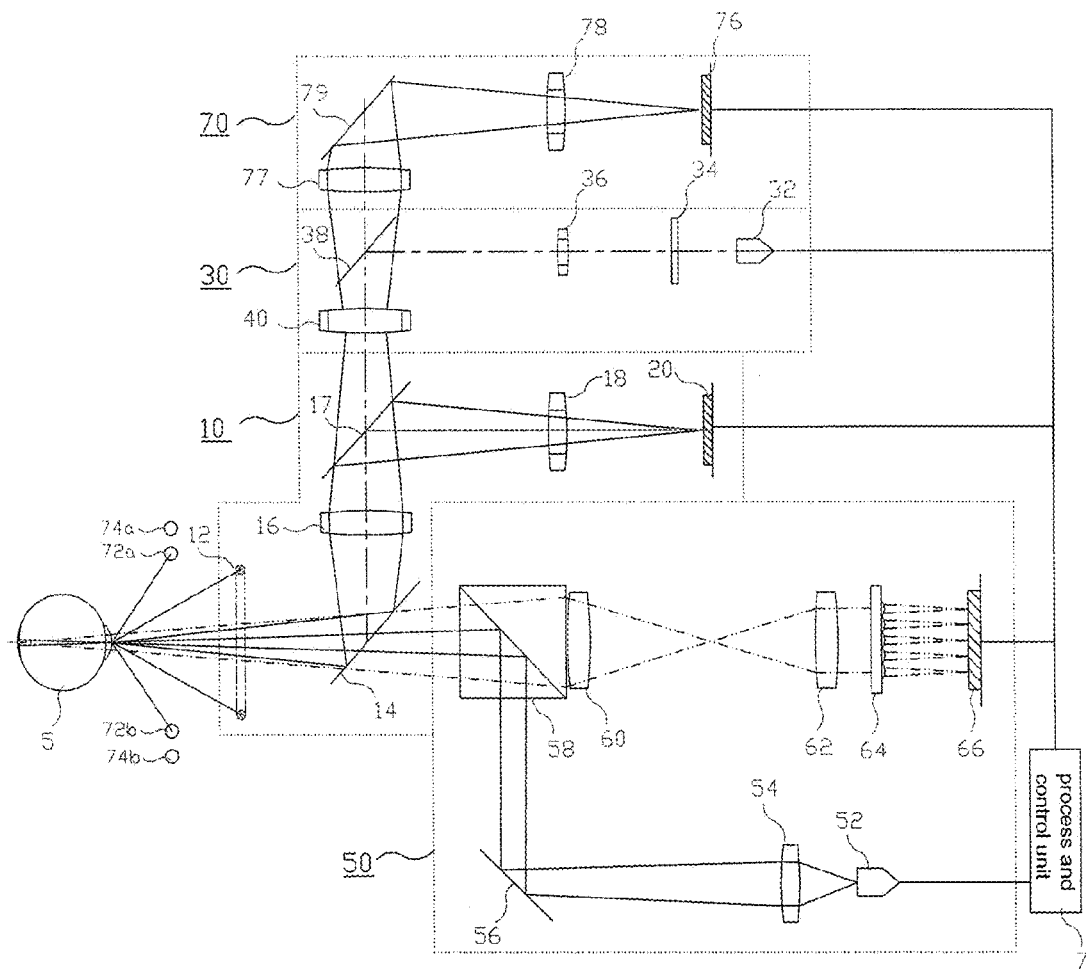
FIG. 6 is an optical circuit showing a configuration of a refracto-keratometer according to an embodiment of the present invention.

FIG. 6 is an optical circuit showing a configuration of a refracto-keratometer according to an embodiment of the present invention. As shown in FIG. 6, the refracto-keratometer of the present invention includes an infrared optical system 10 for examining an alignment of an eye 5 and for measuring a corneal curvature of the eye 5, a fogging optical system 30 for relaxing the eye's accommodation power, a refractive power measuring optical system 50 for measuring a refractive power of the eye 5, and a color observation optical system 70 for obtaining a visible light image of the eye 5 and a contact lens placed on the eye 5. In FIG. 6, same reference numerals are designated to the elements having the same or similar functions with the elements shown in FIG. 1.

In the refracto-keratometer of the present invention, the infrared optical system 10 comprises a mire ring light source 12 for emitting an infrared light of a mire ring shape to the eye 5, and a 2-dimensional imaging device 20 for detecting an image of the infrared light of a mire ring shape reflected by the eye 5. The alignment of the eye 5 can be examined, and the corneal curvature thereof can also be measured with the position and size of the image of the infrared light of a mire ring shape obtained from the 2-dimensional imaging device 20. Optionally, the infrared optical system 10 may further comprise the first dichroic mirror 14, the second dichroic mirror 17, at least one relay lens 16, and an image forming or objective lens 18. The first dichroic mirror 14 separates the infrared light emitted from the mire ring light source 12 from an infrared light for measuring a refractive power which is emitted from an infrared light source 52 of the refractive power measuring optical system 50, and then reflects the mire ring shape infrared light to the 2-dimensional imaging device 20. The second dichroic mirror 17 separates the infrared light emitted from the mire ring light source 12 from a visible light(color light) emitted from the color observation optical system 70 and then reflects the mire ring shape infrared light to the 2-dimensional imaging device 20. The relay lens 16 and the image forming lens 18 are provided for delivering or focusing the mire ring infrared light image. Preferably, an infrared light-emitting-diode (IR LED) is used as the mire ring light source 12 for suppressing a pupil reflex.

The refractive power measuring optical system 50 comprises a measuring light source 52, a micro-lens array 64 and a 2-dimensional imaging device 66. The measuring light source 52 emits a light, preferably an infrared light for measuring the refractive power of the eye 5. The measuring light is reflected by a retina of the eye 5 and then refracted in the eye 5 to form a signal light. The micro-lens array 64 splits the signal light into multiple signal lights and also focuses the split signal lights. The 2-dimensional imaging device 66 detects the images of the split signal lights. A topographical map of the wave fronts of the signal lights can be obtained from the images of the split signal lights, and the refractive power of the eye 5 can be calculated with the topographical map. Optionally, the refractive power measuring optical system 50 may further comprise a badal lens 54, a reflective mirror 56, a polarization beam splitter 58, an objective lens 60 and an image forming lens 62. The badal lens 54 focuses the measuring light on a main surface of the eye 5, the reflective mirror 56 reflects the measuring light from the badal lens 54, and the polarization beam splitter 58 polarizes the measuring light, and reflects the polarized measuring light to the eye 5. The linearly polarized measuring light is reflected and scattered on the retina of the eye 5 to form a signal light, and the signal light is focused by the objective lens 60. The focused signal light converges by the image forming lens 62 to form the image of the signal light of a desirable size.

The fogging optical system 30 includes an image layer 34 for producing an image for fixing the eye's attention and also for relaxing the eye's accommodation power, and an adjusting lens 36 for focusing the image formed by the image layer 34 according to the refractive power of the eye 5. By controlling the adjusting lens 36, the image formed by the image layer 34 is focused or defocused at a focal position of the eye 5 to fix the eye's attention or to relax the eye's accommodation power. Thus, the refractive power of the eye 5 is accurately measured regardless of its accommodation power. Optionally, the fogging optical system 30 may further include relay lenses 40, 16 and dichroic mirrors 14, 17, 38 for delivering, reflecting, focusing or passing the image of the image layers 34. The dichroic mirrors 14, 17, 38 also separate the lights of other optical system 50, 10, 70.

The color observation optical system 70 includes at least one visible light source 72a, 72b, 74a, 74b for emitting at least one visible light to the eye 5 and a 2-dimensional imaging device 76 for detecting the image of the eye 5 formed by the irradiation of the visible light. By using the 2-dimensional imaging device 76, a visible image (a white-and-black image or a color image) of the eye 5 and the contact lens placed on the eye 5 is obtained, and the state of the eye 5 can be clearly examined. Preferably, the visible light source 72a, 72b, 74a, 74b can be a white light source 72a, 72b for emitting a white light for clearly examining (observing) the eye 5, or a blue light source 74a, 74b for emitting a blue light which can clearly detect a dye injected into the eye 5. Instead of the blue light, any visible light, which can detect the dye, for example, which can induce the fluorescence of the dye, can be used. As the visible light source 72a, 72b, 74a, 74b, a light emitting diode (LED) for emitting a visible light can be used. Optionally, the color observation optical system 70 commonly uses some optical elements, such as the first dichroic mirror 14, the second dichroic mirror 17 and the third dichroic mirror 38 with other optical systems 10, 50. The first dichroic mirror 14 reflects the visible light image of the visible light source 72a, 72b, 74a, 74b, the image from the image layer 34 of the fogging optical system 30 and the mire ring shape light image of the infrared optical system 10, but transmits the signal light image of the refractive power measuring optical system 50. The second dichroic mirror 17 reflects the mire ring shape light image of the infrared optical system 10, but transmits the visible light image of the visible light source 72a, 72b, 74a, 74b and the image from the image layer 34 of the fogging optical system 30. The third diachronic mirror 38 reflects the image from the image layer 34 of the fogging optical system 30, but transmits the visible light image of the visible light source 72a, 72b, 74a, 74b. These dichroic mirrors works as a beam splitter, and the reflectance and transmittance of the dichroic mirrors can be determined according to the properties of the optical systems 10, 30, 50, 70. Optionally, the color observation optical system 70 may further include relay or objective lenses 40, 16, 77, 78, and a reflective mirror 79 for delivering, reflecting, focusing or transmitting the visible light images.

Figure 2:
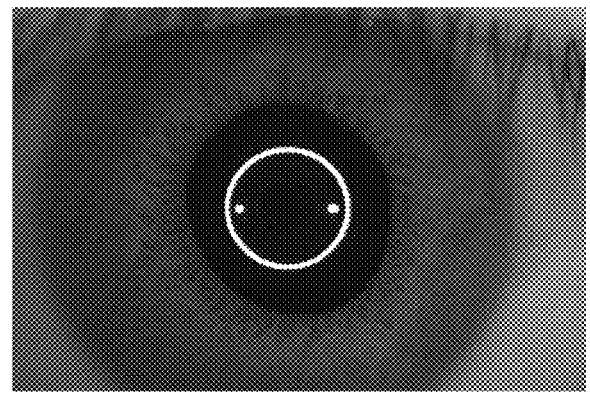
FIG. 2 is a photograph showing an infrared image of an eye for the alignment and the corneal curvature measurement of the eye.
Figure 3:
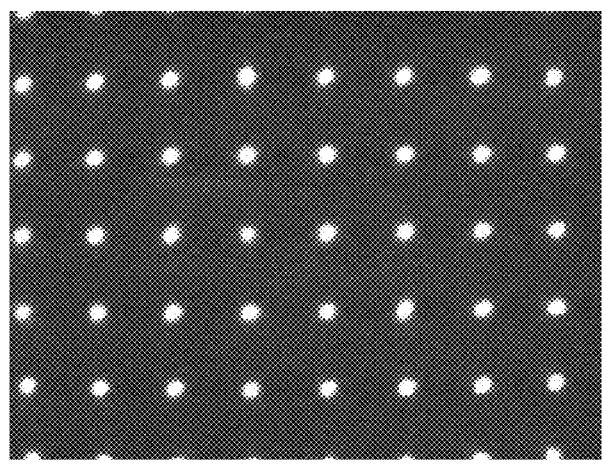
FIG. 3 is a photograph showing images of split signal lights for the measurement of a refractive power of an eye.
Figure 4:
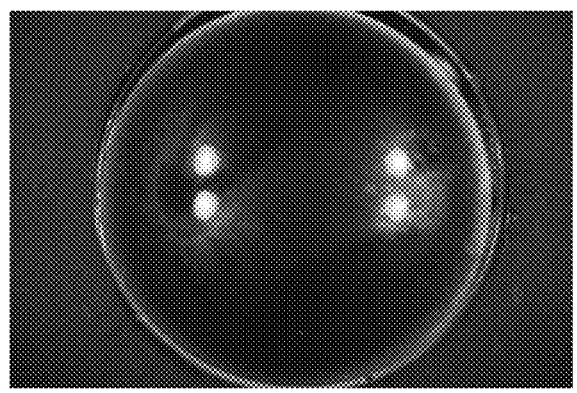
FIG. 4 is a photograph showing an image of an eye to which a fluorescent substance is injected, on which a contact lens is placed, and to which a blue light is irradiated to detect the fluorescent substance for evaluating the fitting state of the contact lens.
Figure 5A:
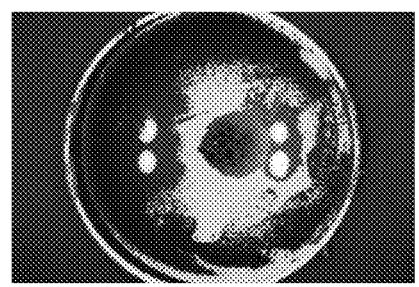
FIGS. 5a~5c are photographs showing the fitting states of a contact lens on a model eye.
Figure 5B:
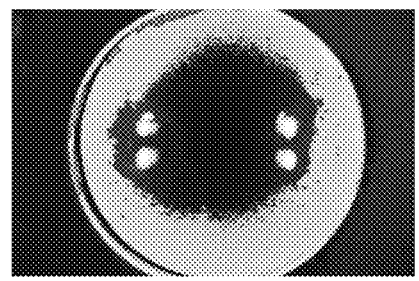
Figure 5C:
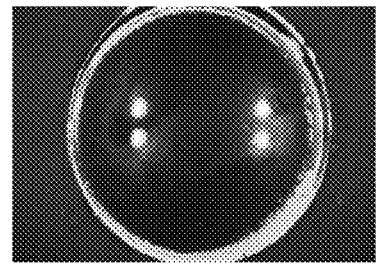

Referring to FIG. 6, the operation of the refracto-keratometer according to the present invention will be explained. According to the control of a process and control unit 7, a mire ring shape infrared light is emitted from the mire ring light source 12 and the mire ring shape infrared light image reflected from the cornea of the eye 5 passes through the first dichroic mirror 14, the relay lens 16, the second dichroic mirror 17 and the objective lens 18, and is detected by the 2-dimensional imaging device 20. Then, the position of the auto ref racto-keratometer is adjusted so that mire ring shape infrared light image is clearly shown, and the center of the mire ring shape infrared light image coincides with the corneal top point of the eye 5 as shown in FIG. 2. Then, the corneal curvature of the eye 5 is calculated by measuring the size of the mire ring shape light image. Next, the refractive power measuring light is emitted from the measuring light source 52 of the refractive power measuring optical system 50. The measuring light passes through the badal lens 54 and the reflective mirror 56, is reflected and linearly polarized by the polarization beam splitter 58, and is focused at the corneal top point of the eye 5. The measuring light forms a light spot of a constant size on the cornea of the eye 5 regardless of the refractive power of the eye 5, and is reflected and scattered on the cornea to be the signal light. The scattered signal light is a non-polarized light and is directed to the polarization beam splitter 58 through the cornea of the eye 5.

In the signal light directed to the polarization beam splitter 58, the signal light having the same polarization direction with the measuring light is reflected by the polarization beam splitter 58 and is directed to the light source 52, and the signal light having the perpendicular polarization direction with the measuring light transmits the polarization beam splitter 58, and is directed to the optical system for measuring the refractive power. The transmitted signal light passes through the objective lens 60 and the image forming lens 64, and is directed to the micro-lens array 64 in a parallel, converging or diverging manner according to the refractive power of the eye 5. At the micro-lens array 64, the signal light is split into multiple signal lights and then converged, and the split signal lights are detected at the 2-dimensional imaging device 66. The refractive power of the eye 5 can be calculated by analyzing the detected image of signal lights. At this time, the fogging optical system 30 relaxes the accommodation power of the eye 5 by defocusing the image for fixing the eye's attention.

Figure 7:
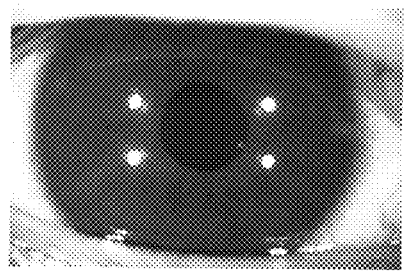
FIG. 7 is a photograph showing an image of an eye which is obtained with the color observation optical system of the ref racto-keratometer of the present invention.

After measuring the corneal curvature and the refractive power of the eye 5, a contact lens is prescribed and placed on the eye 5, and then the fitting state of the contact lens is observed with the color observation optical system 70 of the ref racto-keratometer of the present invention. In detail, a white light is irradiated from a white light source 72a, 72b to the eye 5, and the white light image which is reflected on the eye 5 is transmitted to a 2-dimensional imaging device 76 via the first dichroic mirror 14, the second dichroic mirror 17, the third dichroic mirror 38, relay lenses 16, 40, 77, 78 and a reflective mirror 79. FIG. 7 is a photograph showing the image of the eye 5 which is obtained with the color observation optical system of the refracto-keratometer of the present invention. The eye 5 can be precisely observed with the color (visible light) image shown in FIG. 7. In the next step, a fluorescent substance is applied to the eye 5, for example, by using a fluorescent liquid or a fluorescent paper, and the prescribed contact lens is placed on the eye 5. Then, a visible light, for example, a blue light is irradiated from a blue light source 74a, 74b to the eye 5. The blue light image which is reflected on the eye 5 is transmitted to the 2-dimensional imaging device 76 through the same path of the white light image. At the 2-dimensional imaging device 76, the visible light images of the eye 5 and the contact lens are formed. The blue light emitted from the blue light source 74a, 74b has a superior reactivity to the fluorescent substance, and detects the fluorescent substance well. In a prior method for observing the contact lens fitting state with a slit beam microscope, a blue light is prepared by converting a white light with a blue filter, but such blue light has a inferior reactivity to the fluorescent substance, and a light efficiency of the blue light is not satisfactory. On the other hand, in the present invention, the blue light is directly emitted from the blue light source 74, 74b. Thus, the eye examining apparatus of the present invention has a relatively simple configuration, and is easy to use, and produces a visible light having a superior reactivity to the fluorescent substance.

Figure 8:
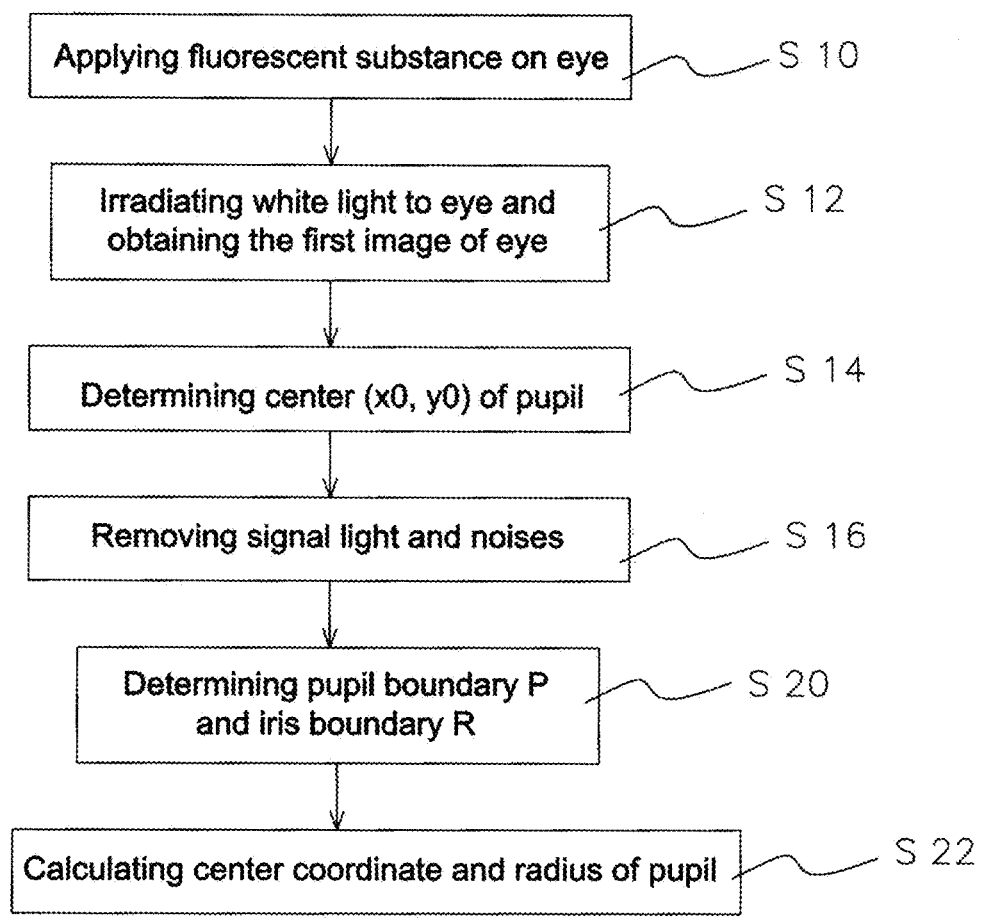
FIG. 8 is a flow chart showing steps for detecting a pupil area and an iris area in an eye.

Hereinafter, the method for evaluating a contact lens fitting state will be explained with reference to FIG. 6. The method for evaluating a contact lens fitting state comprises the steps of (i) detecting a pupil area and an iris area in an eye, and (ii) detecting a fluorescent substance pattern dispersed in the pupil area and the iris area to evaluate the contact lens fitting state. FIG. 8 is a flow chart showing steps for detecting the pupil area and the iris area in an eye. As shown in FIG. 8, a fluorescent substance(dye), such as fluorescein, is applied on an eye (S10), and a contact lens is placed on the eye. Specifically, the fluorescent substance (a dying solution) is applied on a conjunctiva of an eye, which includes a model eye, whose corneal curvature (K) is measured, and the contact lens is placed on the eye or the model eye. The contact lens can be positioned at the top of the cornea of the eye (namely, at the center of the pupil) by blinking an eyelid of the eye. At this state, a white light is irradiated and illuminated to the eye and the first image of the eye is obtained by using the white light source 72a, 72b and the 2-dimensional imaging device 76 (S12). The pupil absorbs most of the white light to produce a dark image, and the brightness of the white light image has the order of pupil<iris<sclera and eyelid. From the first image of the eye, each eye part can be identified.

Figure 9:
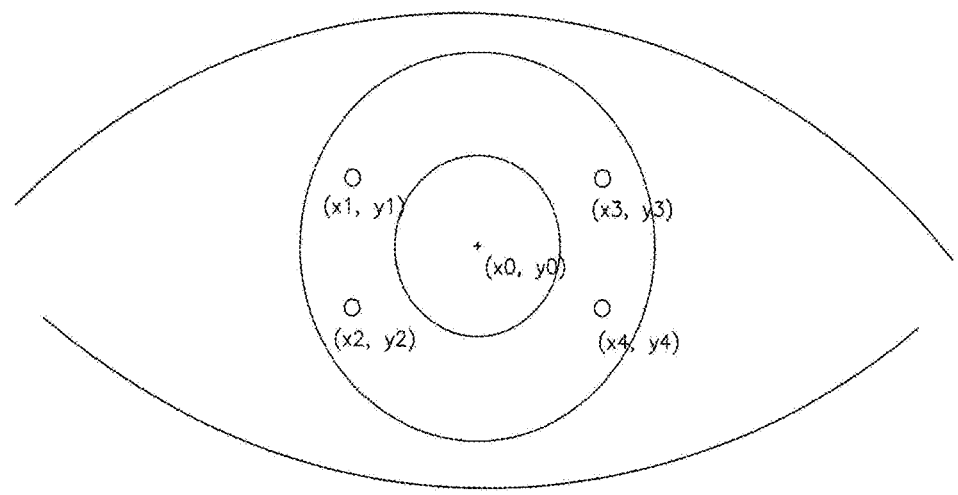
FIG. 9 is a drawing showing an image of an eye to which a white light is irradiated.
Figure 10:
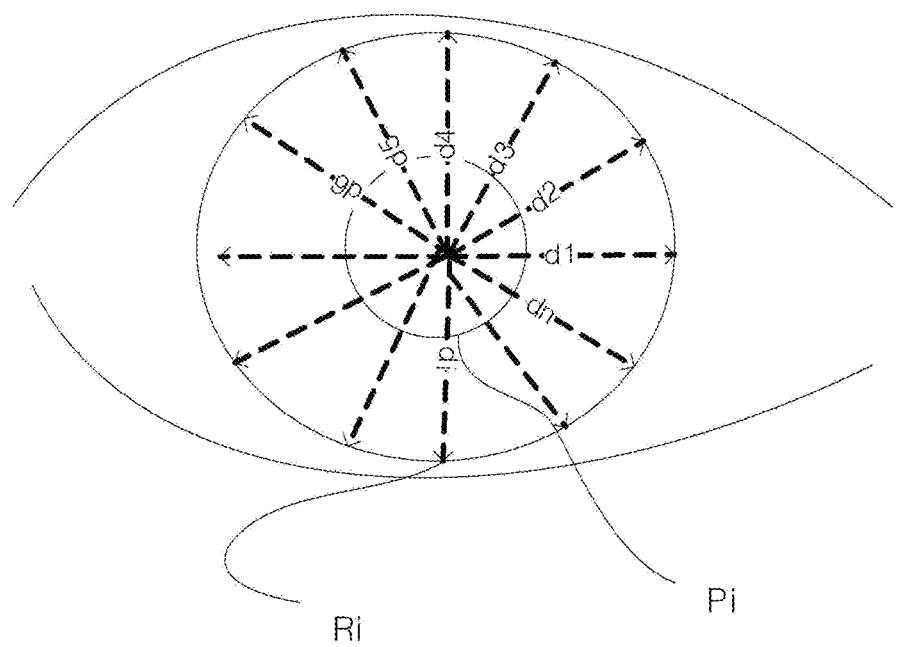
FIG. 10 is a drawing for explaining a process of obtaining a pupil area and an iris area in an image of an eye.

The first image of the eye is obtained as a color image. Optionally, a gray scaling can be applied to the color first image to convert the color information of each pixel into the brightness information (intensity) of each pixel. The pupil area and the iris area are detected with the color first image or the gray scaled first image. FIG. 9 is a drawing showing an image of an eye to which the white light is irradiated. As shown in FIG. 9, the positions (x1, y1), (x2, y2), (x3, y3), (x4, y4) of the 4 images of the white light (signal lights), which is reflected on the eye, are detected, and the center (x0, y0) of the 4 positions is determined as the start point, namely, the center of the pupil (S14). Next, the signal light, and optionally noises is removed from the image of the eye (S16). At this time, the signal light and noises can be removed by conventional image processing techniques, such as a morphology operator, an erosion operator, a dilation operator, a closing operator, and so on. At the boundaries of the pupil, the iris and the sclera, the brightness of the image pixels changes abruptly, and each area (pupil, iris and sclera) can be determined from the differences of the gray levels (brightness) in the areas. For example, the first image is divided into a plurality of pixels which are small enough to differentiate the pupil, the iris and the sclera areas. A gradient mask of 5×5 window size can be used for the pixel formation. Then, as shown in FIG. 10, n radial lines (d1 ... dn) are drawn outwardly from the start point (x0, y0) in the first image of FIG. 9 with a constant angle interval (for example, 15~45 degree). Preferable number of the radial lines(n) is 8~24. On the radial line (di), two edges (boundary points) are determined from the brightness differences wherein the first boundary point Pi is a boundary between the pupil area and the iris area, and the second boundary point Ri is a boundary between the iris area and the sclera area. In other words, the two edges are determined from sudden changes of color levels on the n radial lines (d1 ... dn). Conventional edge-exploring algorithms such as a zero crossing can be applied to obtain the edges. For each of the n radial lines (d1 ... dn), the two edges (boundary points) are determined from the brightness differences to obtain the first boundary P={P1, P2, ... Pi, ... Pn} between the pupil area and the iris area and the second boundary R={R1, R2, ... Ri, ... Rn} between the iris area and the sclera area (S20). The first boundary P corresponds to the pupil boundary, and the second boundary R corresponds to the iris boundary. Then, the center point (Xp, Yp) of the circular first boundary P, namely, the center coordinate of the pupil, and radius of the pupil are calculated from the coordinates of the first boundary P (S22). For the calculations, a conventional circular fitting algorithm can be used.

Figure 11:
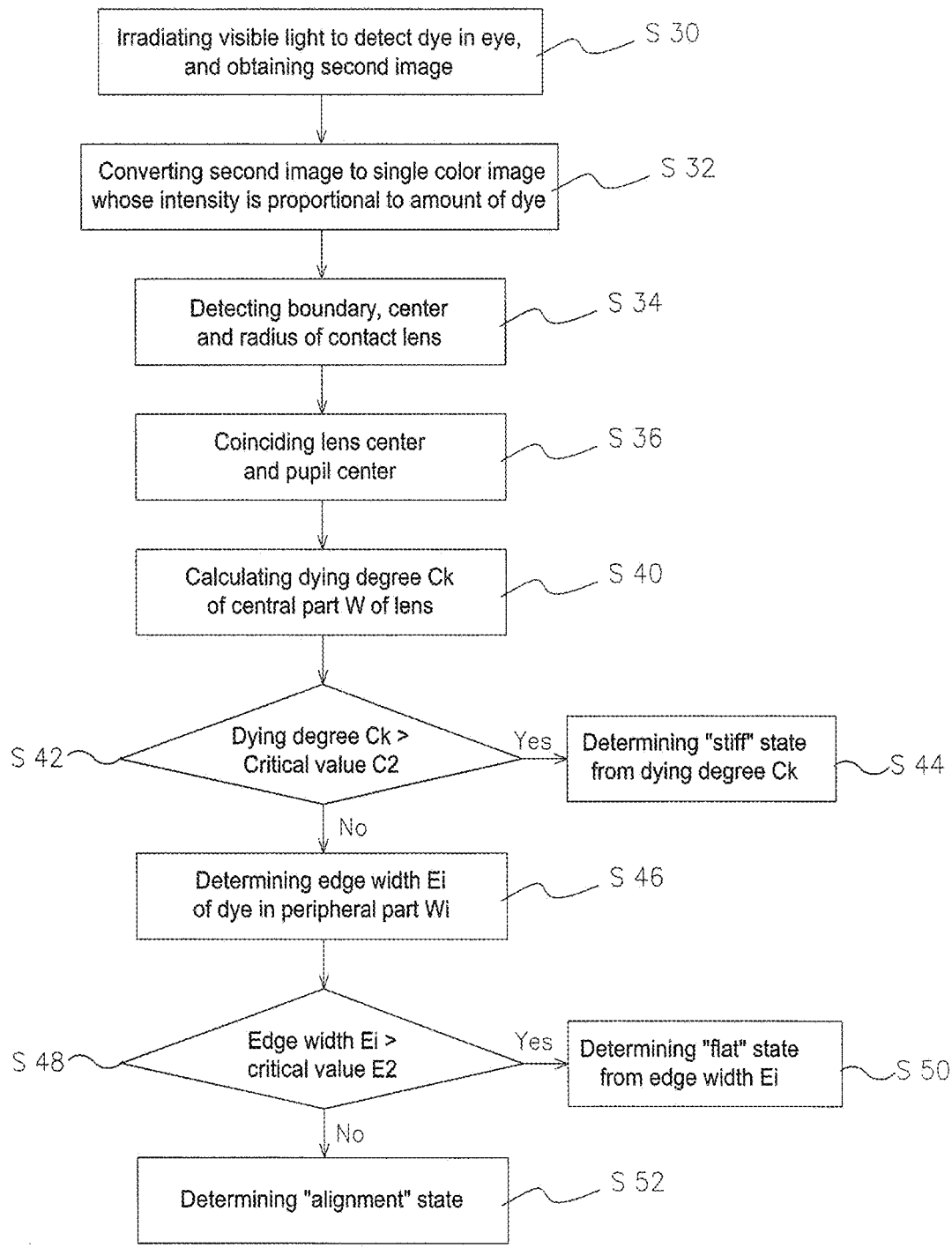
FIG. 11 is a flow chart showing the steps for evaluating a contact lens fitting state by detecting a fluorescent substance pattern dispersed in a pupil area and an iris area according to the present invention.

After detecting the pupil area and the iris area, the contact lens fitting state is evaluated by detecting a fluorescent substance (dying solution) pattern dispersed in the pupil area and the iris area. FIG. 11 is a flow chart showing the steps for evaluating the contact lens fitting state by detecting a fluorescent substance pattern dispersed in the pupil area and the iris area according to the present invention. As shown in FIG. 11, a visible light, which can detect a dye, specifically, the fluorescent substance dispersed in the eye, is irradiated to the eye to obtain the second image (a dye image or a fluorescent substance pattern) of the eye (S30). For example, the visible light can be a blue light irradiated from the blue light source 74a, 74b in FIG. 6, and the fluorescent substance can be the fluorescein. The fluorescein reacts with the blue light to emit a green fluorescent light whose intensity is proportional to the amount of the fluorescent substance dispersed in the eye. When the contact lens curvature is smaller than the corneal curvature ("steep" contact lens), the periphery of the cornea is excessively pressed and the fluorescent substance gathers in the central part of the lens to show a strong green pattern. On the other hand, when the contact lens curvature is larger than the corneal curvature ("flat" contact lens), the center of the cornea is excessively pressed and the contact lens is tightly contacted to the cornea. Thus, the color at the center of the contact lens becomes similar to the color of the pupil, and a ring shaped green pattern is produced at the periphery of the contact lens. In summary, as the contact lens is in the "flat" state or the "steep" state, the fluorescent substance pattern becomes clear and vivid and has its particular shapes. When the contact lens curvature is suitable for the corneal curvature of the eye ("alignment" contact lens), a light green pattern appears in the whole area of the contact lens and a ring shaped green pattern having a narrow width is produced at the periphery of the contact lens.

Figure 12:
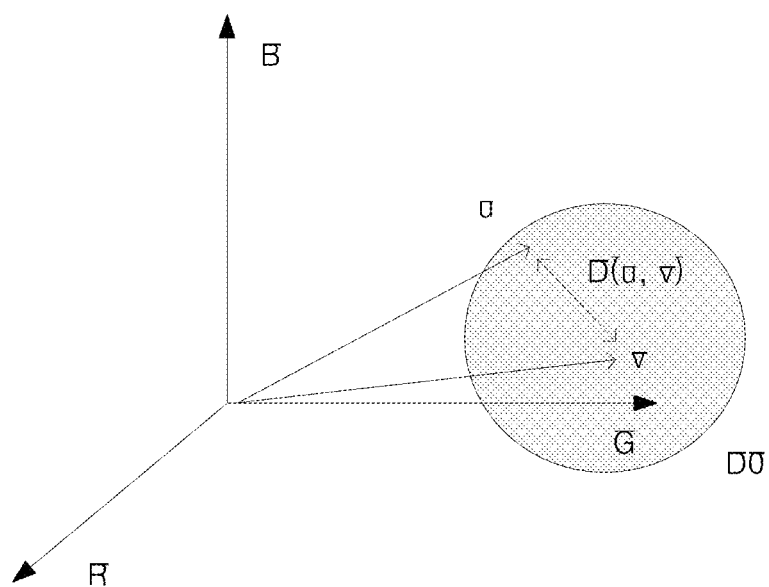
FIG. 12 is a color coordinate system for forming a single color image whose brightness (intensity) is proportional to an amount of a fluorescent substance in one embodiment of the present invention.

After obtaining the second image (dye image) of the eye, the second image is converted to a single color image in which the brightness (intensity) of the single color image is proportional to the amount of the fluorescent substance (S32). FIG. 12 is a color coordinate system for forming the single color image whose brightness (intensity) is proportional to the amount of the fluorescent substance in one embodiment of the present invention. In FIG. 12, the most intrinsic color of the fluorescent substance (dye) is defined by a vector u having respective R, G, B component, and a color of a pixel at position (x, y) in the second image is defined by a vector v. The single color image is formed by calculating a color level (color difference) which corresponds to the distance between the two vectors u and v. Specifically, in the RGB color coordinate system, as the Euclidean distance D(v,u) between the two end points of the two vectors u and v becomes smaller, the image of the corresponding pixel becomes more similar to the intrinsic color (for example, a vivid green color) of the fluorescent substance, and a larger amount of the fluorescent substance exists in the corresponding pixel. Thus, under the condition that D(u,v) is less than a critical value D0, a standardized color level g(x, y) can be defined in a range of 1 to 255 which is inversely proportional to the magnitude of D(u, v). Thereby, in a 2-dimensional plane corresponding to the second image, the standardized color level g(x, y) can be used in place of the original RGB color value for each pixel. By these procedures, the color second image is converted to a single color (color of the fluorescent substance) image. In summary, the dye image is converted to the single color image by obtaining the standardized color level g(x, y) which corresponds to the distance between two vectors u and v. By such scaling process, the contrast of the second image can be adjusted in a desirable level, the RGB color information of 3 byte is converted into a single color information of 1 byte. Therefore, the dye pattern can be easily and quickly detected and analyzed.

Figure 13:
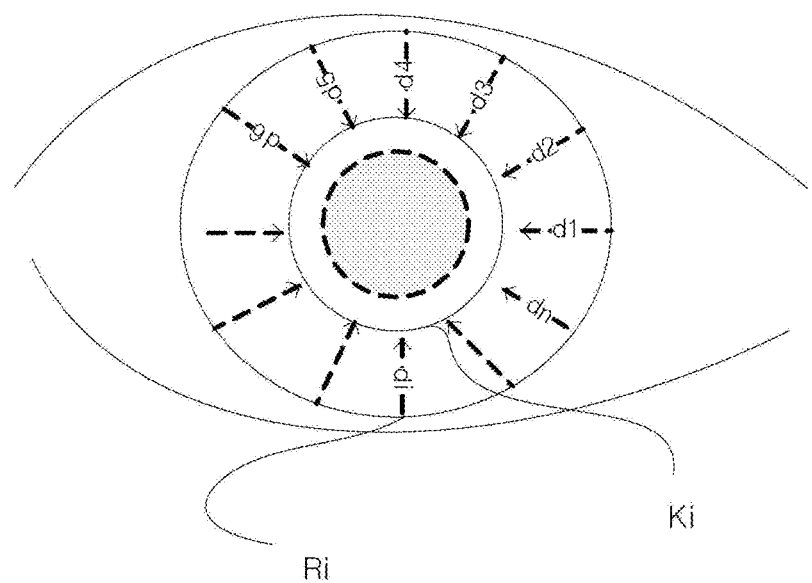
FIG. 13 is a drawing for explaining a process of obtaining a boundary of a contact lens from a single color image of an eye and a contact lens.

In the next step, a boundary, a center and a radius of the contact lens placed on the eye is detected from the single color image in which the brightness (intensity) of each pixel is proportional to the amount of the fluorescent substance (S34). FIG. 13 is a drawing for explaining a process of obtaining the boundary K of the contact lens from the single color image of the eye and the contact lens. As shown in FIG. 13, in the single color second image, n radial lines (d1 ... dn) are formed from the second boundary R={R1, R2, ... Ri, ... Rn} between the iris area and the sclera area to the center (Xp, Yp) of the pupil area. On the n radial lines (d1 ... dn), edges (boundary points, K1, K2, ... Ki, ... , Kn) are determined from the sudden changes of color level, in other words, from the brightness differences of the single color, and the determined edges form a lens boundary K. In determining the lens boundary K, conventional edge-exploring algorithms, which are used for determining the pupil area and the iris area, can be used. Then, from the coordinates of the lens boundary K={K1, K2, ... Ki, ... , Kn}, the center (X1, Y1) and radius Rc of the contact lens are determined.

Meanwhile, according to the fitting state between the eye and the contact lens, there is a possibility that the fluorescent substance is not concentrated at the edge (actual boundary) of the contact lens. In this case, to determine the more accurate lens boundary and lens center, the following circle detecting method can be further applied. In the single color second image produced with the standardized color level g(x, y), an arbitrary lens center (X1, Y1) is determined, and the color(for example, green) levels of all pixels at a circumference which is apart from the center (X1, Y1) by a radius r are divided by $2\pi r$ for a normalization. Then, the rate of change of the normalized color levels with respect to the radius r is determined. When the rate of change of the normalized color levels is maximized at a lens center (Xc, Yc) and at a lens radius Rc, the lens center (Xc, Yc) and the lens radius Rc can be used as the more accurate lens information. In other words, a sum of the normalized color (green) levels at the pixels which are positioned at the circumference of at radius r is obtained. The sums are obtained for various r, and the rate of changes of the green levels with respect to the various radius r are determined from the sums. At a specific radius Rc, the rate of change is maximized, and the radius Rc and its center are used as the real contact lens information. If the distance between the lens center (X1, Y1) or (Xc, Yc) and the pupil center (Xp, Yp) is larger than a predetermined value, namely, if the contact lens is positioned at a wrong position, it is desirable to coincide the lens center (X1, Y1) or (Xc, Yc) and the pupil center (Xp, Yp) by adjusting the position of the contact lens (S36).

Figure 14:
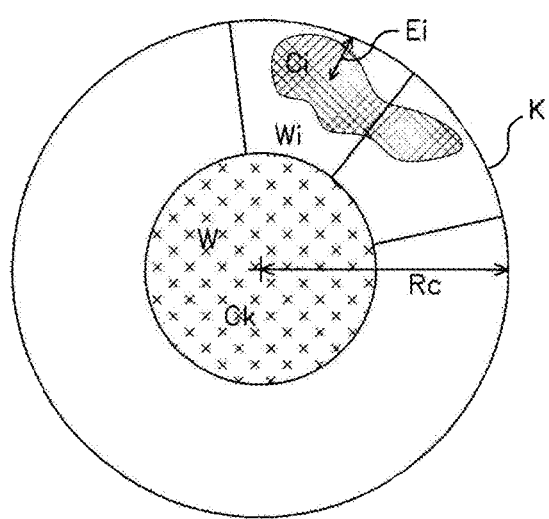
FIG. 14 is a drawing for explaining a process of detecting a fluorescent substance dispersion pattern in a contact lens area.

Next, the contact lens fitting state is evaluated by detecting the fluorescent substance dispersion pattern in the contact lens area. FIG. 14 is a drawing for explaining a process of detecting the fluorescent substance dispersion pattern in the contact lens area. As shown in FIG. 14, the contact lens area K is divided into two parts, a central part W and peripheral parts (W1, W2, . . . , Wi, . . . , Wn). The central part W is the inner circle area having a radius of ¼ to ½ times, preferably ⅓ times of the contact lens radius Rc from the contact lens center (X1, Y1). The peripheral part (W1, W2, . . . , Wi, . . . , Wn) Is the remaining part surrounding the central part W. Then, a dying degree Ck of the central part W is calculated (S40), and the calculated dying degree Ck is compared with a predetermined range to evaluate the contact lens fitting state. Preferably, the dying degree Ck of the central part W is a ratio of (i) an area of pixels Wg having a color intensity (green level) of more than a predetermined value (namely, pixels including effective amount of the fluorescent substance) with respect to (ii) the area of the central part W. Alternatively, the dying degree Ck can be an average color intensity (green level) of pixels having a color intensity of more than a predetermined value. The calculated dying degree Ck is compared with a critical value C2(S42), wherein a standard dying degree is C1~C2 when the distance between the central part W of the contact lens and the cornea of the eye is suitable. When the dying degree Ck is larger than the critical value C2, it is determined that the lens curvature is in a "stiff" state, and the stiff degree is determined from the difference between the dying degree Ck and the critical value C2 (S44).

On the other hand, the peripheral parts of the contact lens includes n areas (W1, W2, . . . Wi . . . Wn), and a dying degree Ci is calculated for each peripheral part Wi, for example, by the above mentioned procedure. Then, an edge width of fluorescent substance pattern Ei is determined (S46), wherein the edge width Ei is a minimum distance from a center of gravity of pixels having color intensity (green level) of more than a predetermined value in the peripheral part Wi to the lens boundary. The calculated edge width Ei is compared with a critical value E2 (S48), wherein a standard edge width is E1~E2 when the contact lens fitting state is suitable. When the edge width Ei is larger than the critical value E2, it is determined that the lens curvature is in a "flat" state, and the flat degree is determined from the difference between the edge width Ei and the critical value E2 (S50). Alternatively, the dying degree Ci for peripheral part Wi is compared with critical values C3 and C4 to determine the stiff or flat state of the lens, wherein a standard dying degree is C3~C4 when the distance between the peripheral part Wi of the contact lens and the cornea of the eye is suitable. When the dying degree Ck, Ci is within the standard ranges in the central part and the peripheral parts of the contact lens, or the edge width Ei is within the standard range in the peripheral parts, namely, when the contact lens is not in a steep or flat state, it is determined that the lens curvature is in an "alignment" state (S52). If necessary, from the corneal curvature obtained with the refracto-keratometer and the obtained fitting state (stiff or flat degree), a base curve value K' of the contact lens suitable for the eye can be calculated.

While the present invention has been shown and described with reference to certain preferred embodiments thereof, it will be understood by those skilled in the art that various changes in form and details may be made therein without departing from the spirit and scope of the invention as defined by the appended claims.

The invention claimed is:

1. A method for evaluating a contact lens fitting state, the method comprising the steps of:
   detecting a pupil area and an iris area in an eye;
   obtaining a dye image showing a location of a dye in the eye by irradiating a visible light which can detect the dye to the eye;
   converting the dye image to a single color image whose color levels are proportional to amounts of the dye;
   detecting a boundary, a center and a radius of a contact lens placed on the eye from the single color image;
   dividing an area of the contact lens into two parts, a central part W and peripheral parts W1, W2, . . . Wi . . . Wn, the central part W being an inner circle area having a radius of ¼ to ½ times of the radius of the contact lens and the peripheral parts W1, W2, . . . Wi . . . Wn being the remainder of the central part W; and
   calculating a dying degree Ck of the central part W and comparing the calculated dying degree Ck with a predetermined range to evaluate the contact lens fitting state,
   wherein the single color image is formed by calculating a standardized color level g(x, y) which corresponds to a distance between two vectors u and v,
   wherein the most intrinsic color of the dye is defined by a vector u, and a color of a pixel at position (x, y) in the dye image is defined by a vector v, and
   wherein the dying degree Ck is a ratio of an area of pixels Wg having color levels that are higher than a predetermined value in the central part W with respect to the area of the central part W in the single color image.

2. The method of claim 1, further comprising a step of evaluating the contact lens fitting state by
   calculating a dying degree Ci of the peripheral part Wi,
   calculating an edge width Ei which is a minimum distance between a center of gravity of pixels having color levels higher than a predetermined value in the peripheral part Wi and the boundary of the contact lens, and
   then comparing the dying degree Ci and the edge width Ei with predetermined ranges.

3. The method of claim 1, further comprising a step of evaluating the contact lens fitting state by calculating a dying degree Ci of the peripheral part Wi, and then comparing the dying degree Ci with a predetermined range.

4. The method of claim 1, wherein the step of detecting the boundary of the contact lens includes the steps of
   forming n radial lines (d1 . . . dn) from a boundary between the iris area and a sclera area of the eye to the center of the pupil area in the single color image of the eye,
   determining edges from sudden changes of color levels on the n radial lines (d1 . . . dn), and
   obtaining the lens boundary from the determined edges on the n radial lines (d1 . . . dn).

5. The method of claim 1, wherein the step of detecting the pupil area and the iris area includes the steps of
   irradiating and illuminating a white light to the eye to obtain the eye's image, forming n radial lines (d1 . . . dn) outwardly from a center of the pupil in the eye's image, determining two edges from sudden changes of color levels on the n radial lines (d1 . . . dn), and obtaining the pupil area and the iris area from the determined two edges on the n radial lines (d1 . . . dn).

* * * * *